US007213320B1

(12) United States Patent
Holmquist et al.

(10) Patent No.: US 7,213,320 B1
(45) Date of Patent: May 8, 2007

(54) MOISTURE BARRIER CONE

(75) Inventors: John P. Holmquist, Indian Harbor Beach, FL (US); Alejandro Mancuso, Orlando, FL (US); Par Ostberg, Winter Park, FL (US); Par Axelsson, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 11/478,880

(22) Filed: Jun. 30, 2006

Related U.S. Application Data

(62) Division of application No. 10/738,540, filed on Dec. 17, 2003, now Pat. No. 7,168,102.

(60) Provisional application No. 60/434,023, filed on Dec. 17, 2002.

(51) Int. Cl.
*B21D 39/03* (2006.01)
*A61F 9/02* (2006.01)
*A62B 39/03* (2006.01)

(52) U.S. Cl. ....................... 29/428; 2/435; 128/201.15; 128/201.29

(58) Field of Classification Search .................... 2/455, 2/456, 457, 458, 2.11, 2.14, 2.15, 2.17, 410, 2/5, 6.1, 6.3, 8.2, 8.6, 424, 427, 435, 205, 2/901, 909, 918, 202; 128/201.22, 206.23, 128/201.23, 202.11, 201.24, 203.29, 201.29, 128/206.22, 201.15
See application file for complete search history.

(56) References Cited

U.S. PATENT DOCUMENTS 1,079,955 A * 12/1913 Scheidegger ................. 29/428
1,151,342 A * 8/1915 Cohn .......................... 29/428
1,570,128 A * 1/1926 Carter ......................... 29/428
2,649,583 A 8/1953 Schaeffer ........................ 2/458
2,665,686 A 1/1954 Wood et al. ................ 128/141
2,709,667 A 5/1955 Grubb et al. ................. 154/44
2,799,862 A 7/1957 Rowe ................................ 2/9
2,821,192 A 1/1958 Monro ....................... 128/141
2,891,541 A 5/1959 Tietze ........................ 128/141
2,936,458 A 5/1960 Luisada ......................... 2/435

(Continued)

FOREIGN PATENT DOCUMENTS

FR 2608932 12/1986

*Primary Examiner*—Rodney Lindsey
(74) *Attorney, Agent, or Firm*—Brian S. Steinberger; Phyllis K. Wood; Law Offices of Brian S. Steinberger, P.A.

(57) ABSTRACT

Closed air space devices and methods of use for full body bio hazard type suits that eliminates condensation and fogging from forming on the face masks and the window visors of the suit. The devices and methods have a sealed closed air space that can be formed from flexible see-through plastic in a cone shape that can be sealed between the mask and the visor. The closed air space can be pre-sealed to the visor/outer wall of the suit and have a second end fitted with an elastic type band that allows the wearer to attach and detach the closed space by wrapping the band about their face mask. Other embodiments use flat see-through plastic sheets, and sheets that attach about the neck of the user to form the closed air spaces between the face mask and the window visor of the suit.

6 Claims, 7 Drawing Sheets

U.S. PATENT DOCUMENTS

| | | | | | |
|---|---|---|---|---|---|
| 3,172,126 | A | | 3/1965 | Spano | 2/410 |
| 3,377,626 | A | | 4/1968 | Smith | 2/14 |
| 3,534,408 | A | | 10/1970 | Fifield | 2/2.17 |
| 3,559,642 | A | | 2/1971 | Cupp | 128/142.5 |
| 3,591,864 | A | | 7/1971 | Allsop | 2/14 K |
| 3,911,913 | A | * | 10/1975 | June | 128/201.29 |
| 4,484,575 | A | * | 11/1984 | Brockway et al. | 128/201.23 |
| 4,561,162 | A | * | 12/1985 | Brockway et al. | 29/428 |
| 5,054,479 | A | | 10/1991 | Yelland et al. | 128/201.25 |
| 5,095,550 | A | | 3/1992 | Perlinger | 2/422 |
| 5,802,609 | A | | 9/1998 | Garofalo | 2/2.17 |
| 5,991,921 | A | | 11/1999 | Saito | 2/69 |
| 6,266,828 | B1 | | 7/2001 | Corsini | |
| 2005/0010996 | A1 | * | 1/2005 | Steinert | 2/458 |

* cited by examiner

MOISTURE BARRIER CONE

This is a Divisional of application Ser. No. 10/738,540 filed Dec. 17, 2003 now U.S. Pat. No. 7,168,102 which claims priority of U.S. Provisional Application 60/434,023 files Dec. 17, 2002.

FIELD OF INVENTION

This invention relates to body protection suits, and in particular to condensation prevention devices, and methods of using the devices, that prevent fogging of the viewing windows in fully enclosed body suits such as bio hazard suits, and the like, and prevents fogging on face masks worn by users wearing the body suits.

BACKGROUND AND PRIOR ART

Emergency workers such as firefighters, and the like, and workers that handle biological and hazardous materials, often require the use of full body suits for their work, such as type Level A and Level B Suits. A Level A Suit is a suit worn when the highest level of skin, respiratory, and eye protection against chemicals is needed. The suit consists of a totally encapsulating, vapor-protective ensemble worn with a self-contained breathing apparatus (SCBA) when the environment in which tasks have to be performed presents immediate danger to life and health (IDLH) hazard at both a respiratory and skin contact and impairs a worker's ability to escape. The level B Suit is worn when the highest level of respiratory protection is required but a lesser level of skin protection is needed. The suit consists of a chemical liquid splash protective suit worn with an SCBA when the environment presents an IDLH inhalation hazard, but does not present a skin contact hazard nor does it impair a worker's ability to escape. These full body suits have been known to have condensation problems that seriously affect their usefulness.

A common problem with these suits is that the masks worn by the workers and/or the visors on the suit become fogged within approximately five minutes of use. The build up of condensation on the visors and/or masks reduces the worker's visibility so as to not allow the worker to effectively perform the precision tasks required in their jobs. This lack of visibility causes which reduces the operating time of the workers and can become fatal when working in environments having smoke, hazardous chemicals and the like. Additionally, it is a known fact that firefighters and emergency type workers can only stay in their suits for approximately twenty minutes, due to the air supply and the heat conditions from typical fires that can lead to dehydration. That means that every second is valuable for the limited amount of time that the firefighter and emergency worker can wear their suits. Thus, the decreased visibility and high degree of body heat will shorten the working time in the suit and will have drastic effects on the effectiveness of the person wearing the suit.

The typical technique of handling the condensation problem is for the firefighters to carry towels which are used to wipe clean the mask and the visor of the suit. Based on the condensation problem, the firefighter would typically have to clean their masks and/or visors every five minutes while they are fighting a fire. However, to use the towels, the firefighter would have to open their suits exposing their bodies to the dangerous environment which they are in. Alternatively, the firefighter would have to leave the fire to clean their masks and/or visors every seven minutes. Furthermore, the towel solution is also problematic because the user must spend time to wipe the condensation away, which reduces the time spent on their work tasks. Also, the user must carry the towel which also takes up valuable space and one of the valuable hands of the user which takes away the effectiveness of the worker performing their work.

Various types of modified body suits that include fluid chilled systems, pre-chilled or forced air systems, passive cooling systems, ice or gel or cool packs, evaporative cooling, and environment cooling systems have been developed to deal with condensation problems, but come with their own problems. Many of these added on components can be expensive, require electricity and batteries to operate. Additionally, many of these added on systems have moving parts that require regular maintenance. Mobility with these modified suits is often limited because of having separate components, such as the reservoir and pump are which are separate from the suit garment. These modified suits also can add substantial weight to the body which can tire and slow down the effectiveness of the user. Further, these add on systems, and components take up precious space which further can limit the length of operation of users wearing the modified suits. Still furthermore, these added on component systems are often uncomfortable to wear, require additional undergarments, and can be cold and damp to the wearer of the modified suits further adding to the discomfort of their use.

Anti-fogging solutions such as products such as RainEx® and the like, can be used on the masks and/or visors. However, these solutions only delay when condensation occurs. For example, the RainEx® product has been tested to delay the start of condensation which causes the fogging effect only up to approximately seven minutes, which means that the masks and/or visors still have to be wiped clean with towels after seven minutes instead of after five minutes.

Thus, the need exists for solutions to the above problems.

SUMMARY OF THE INVENTION

A primary objective of the present invention is to provide a method and device that allows workers to continuously work in their body suits such as biological and material hazard suits, space suits, diving suits, and the like, without having to wipe off condensation from their masks and visors.

A secondary objective of the present invention is to provide a method and device that allows workers to continuously work in body suits such as biological and material hazard suits, space suits, diving suits, and the like, without having to use anti-fogging solutions on their masks and visors.

A third objective of the present invention is to provide a method and device that eliminates fogging effects on masks and window visors on body suits such as biological and material hazard suits, space suits, and diving suits.

A fourth objective of the present invention is to provide a method and device that allows workers to continuously wear body suits, such as biological and material hazard suits, space suits, and diving suits for up to approximately 20 continuous minutes at a time without condensation and fogging effects on face masks and window visors.

Various antifogging devices and methods of using the devices are for body safety suits having a head suit portion that covers a head of a worker, and a body suit portion which encompasses a full body of a worker below the head, and includes a face mask for attaching to a face portion of the worker, the head suit portion having a window portion in front of the facemask.

The novel devices and methods include forming a closed air space formed directly between the face mask and the window portion of the body suit, wherein the closed air space eliminates condensation from forming on the face mask of the body suit.

The body safety suits can be selected from a hazardous material suit and a bio hazard suit. Alternatively, the body suit can include a firefighter suit. Alternatively, the body suit can include a space suit. Alternatively, the body suit can include a diving suit.

A first embodiment of the closed air space can include a flexible see-through plastic housing sealingly attached to both the face mask and to the window portion of the suit, wherein the housing has a substantially cone shape. A first end of the housing can include an elastic-stretchable member which sealingly wraps about a portion of the face mask, so that the plastic housing is removably attached to the face mask.

Alternatively, the first end can include a fastener selected from at least one of: hook and loop fasteners, snap fasteners, and a zipper, wherein the fastener sealingly attaches the plastic housing to the face mask, so that the plastic housing is removably attached to the face mask.

The housing can include a second end which is attached to the body suit adjacent to the window visor. The second end can include permanently affixing and sealing the plastic housing to an interior surface of the body suit adjacent to the window portion of the body suit.

Alternatively, the second end can include an elastic-stretchable member which sealingly wraps about a portion of the interior surface of the body suit adjacent to the window portion, so that the plastic housing is removably attached.

Still furthermore, the second end can be a fastener selected from at least one of: hook and loop fasteners, snap fasteners, and a zipper, wherein the fastener sealingly attaches the plastic housing to an interior portion of the body suit adjacent to the window portion, so that the plastic housing is removably attached.

A second embodiment of the invention can include a see-through plastic sheet with a substantially semi-circular configuration having a central portion with an opening which sealingly attaches to the face mask, and upper perimeter edge portions which sealingly attaches to an interior surface of the head suit portion above and below the head of the worker.

The central portion of the sheet can have an elastic-stretchable member which sealingly wraps about a portion of the face mask, so that the plastic sheet is removably attached to the face mask.

Alternatively, the central portion of the sheet can include a fastener which sealingly attaches to a portion of the face mask so that the plastic sheet is removably attached to the face mask, the fastener is selected from at least one of: hook and loop fasteners, snap fasteners, and a zipper fastener.

Alternatively, the upper perimeter edge portions of the sheet can include a fastener selected from at least one of: hook and loop fasteners, snap fasteners and a zipper fastener, so that the sheet can be removable to the inside of the head portion of the suit.

A third embodiment of the closed air space can include a see-through plastic sheet with a substantially semi-circular configuration having a central portion with an opening which sealingly attaches to the face mask, and upper perimeter edge portions which sealingly attaches to an interior surface of the head suit portion behind the head of the worker.

The closed air space can include a see-through plastic bag which is part of the head suit portion; and a neck portion fastener which sealingly attaches the bag to the body suit portion. The neck portion fastener can have an elastic-stretchable member which sealingly wraps about an upper portion of the body suit portion, so that the plastic sheet is removably attached to the face mask.

Alternatively, the neck portion fastener can include a fastener selected from at least one of: hook and loop fasteners, snap fasteners and a zipper fastener.

The third embodiment can also have a moist air exhaust line for exhausting air from the face mask to outside the bag.

The novel invention can include the steps of forming a closed air space between the face mask and the window of the suit, and eliminating condensation from forming on the face mask and the window as the suit is being worn during an emergency condition with the closed air space, using the embodiments described above. Tests using the novel invention has demonstrated eliminating condensation from forming on the face mask and the window visor of the body suit that last at least approximately 20 minutes of the time a worker is wearing the body suit.

Further objects and advantages of this invention will be apparent from the following detailed description of the presently preferred embodiments which are illustrated schematically in the accompanying drawings.

DESCRIPTION OF THE PREFERRED EMBODIMENTS

Before explaining the disclosed embodiments of the present invention in detail it is to be understood that the invention is not limited in its application to the details of the particular arrangements shown since the invention is capable of other embodiments. Also, the terminology used herein is for the purpose of description and not of limitation.

First Embodiment

Figure 1A:
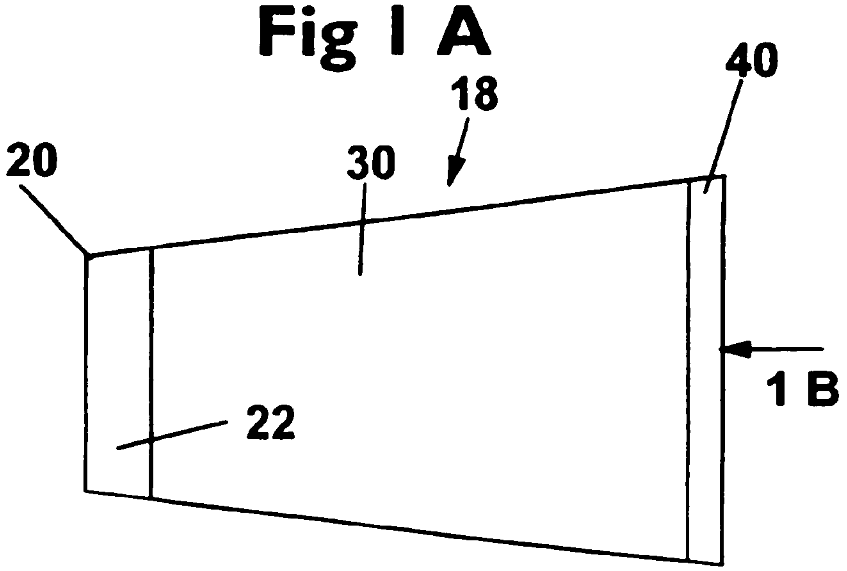
FIG. 1A is a side view of a preferred cone shaped air space for the invention.
Figure 1B:
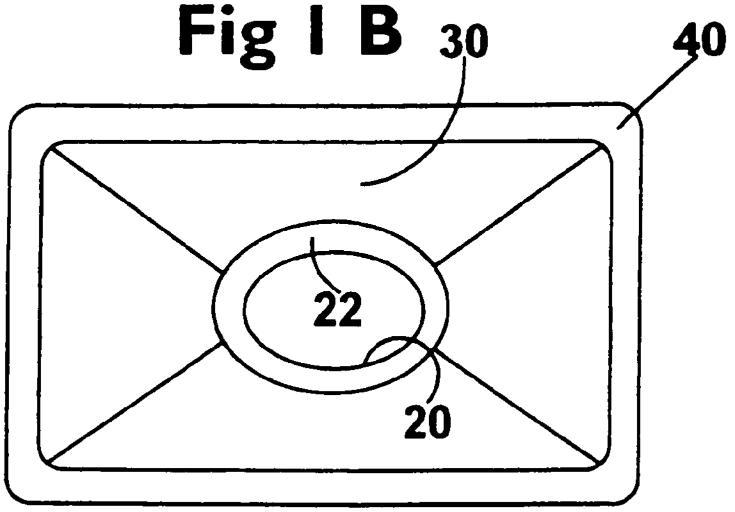
FIG. 1B is an end view of the cone shaped air space of FIG. 1A along arrow 1B.
Figure 1C:
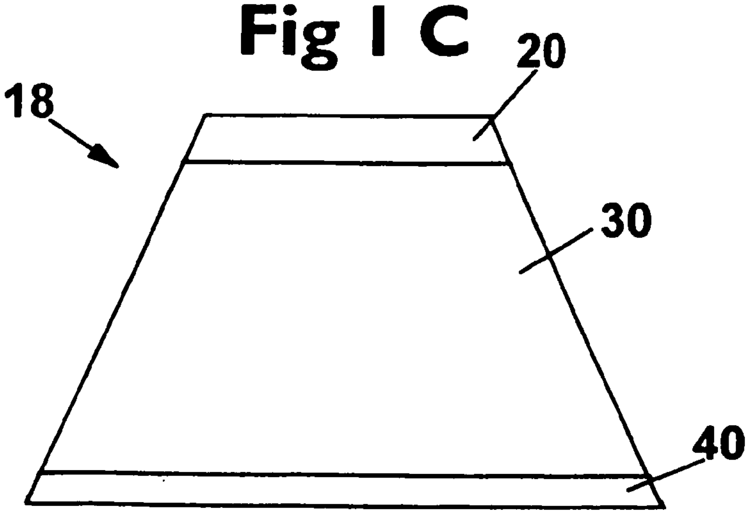
FIG. 1C is another side view of the cone shaped air space of FIG. 1A.

FIG. 1A is a side view of a cone shaped air space 18 for the invention. FIG. 1B is an end view of the cone shaped air space device 18 of FIG. 1A along arrow 1B. FIG. 1C is another side view of the cone shaped air space 18 of FIG. 1A. The cone shaped air space device 18 can include a face mask attachment end 20 having a face mask attaching member such as a flexible elastic band portion 22, such as a rubber type band having a generally ring shaped configuration. The cone shaped air space device 18 can further include an outwardly expanding midportion 30 being in a generally cone shape, that can be formed from a flexible see-through plastic sheathing, and a suit window attachment end 40, which will be described in greater detail below.

Figure 2:
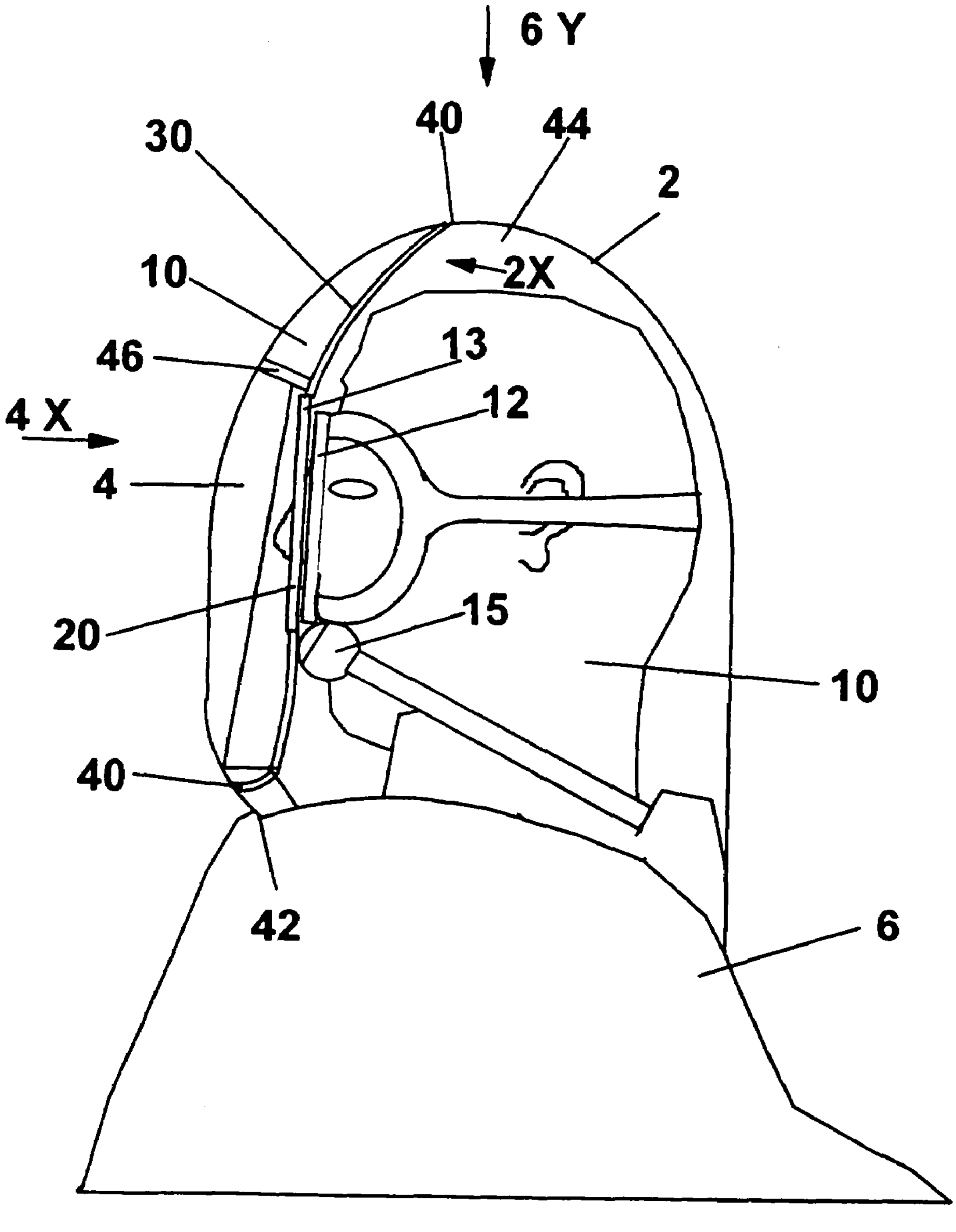
FIG. 2 is a side cross-sectional view of the bio hazard suit and cone shaped air space of the preceding figures attached to a mask worn by a worker.

FIG. 2 is a side view of novel cone shaped air space device 18 of FIGS. 1A–1C used with a full body hazard/bio suit 1 having head portion 2 with window visor portion 4, that is attached to lower body portion 6 such as those described in the background section of the invention. The worker wearing the suit 1 can normally breath by an oxygen breathing apparatus 15, such as those worn by scuba divers and the like. With the invention, the head 10 of a worker can wear a typical face mask 12 having a raised perimeter edge 13 about a visor portion that allows for the attachment end 20 of the cone shaped device 18 to be attached thereto, by stretching the elastic band over and about the perimeter edge 13 of the face mask 12 so that a tight air seal is formed with the cone shaped device 18. Opposite attachment end 40 of the cone shaped device can be pre-sealed to the head portion 2 of the suit 1 adjacent to the window visor 4 by vulcanized, sewn, and the like. Connection points 42, 46 can be along the perimeter edge of the window visor 4. Alternatively, the connection points 44 can be along other inner surface areas of the head portion 2, such as along the top inner surface of the head portion 2 directly above the worker 10. Here, the novel cone shaped device 18 forms a closed air space between the face mask visor 12 and the window visor 4 on the bio hazard suit 1, and as shown in FIG. 5 eliminates moisture such as condensation from forming on both the face mask visor 12 and on the window visor 4 of the suit 1.

Figure 3:
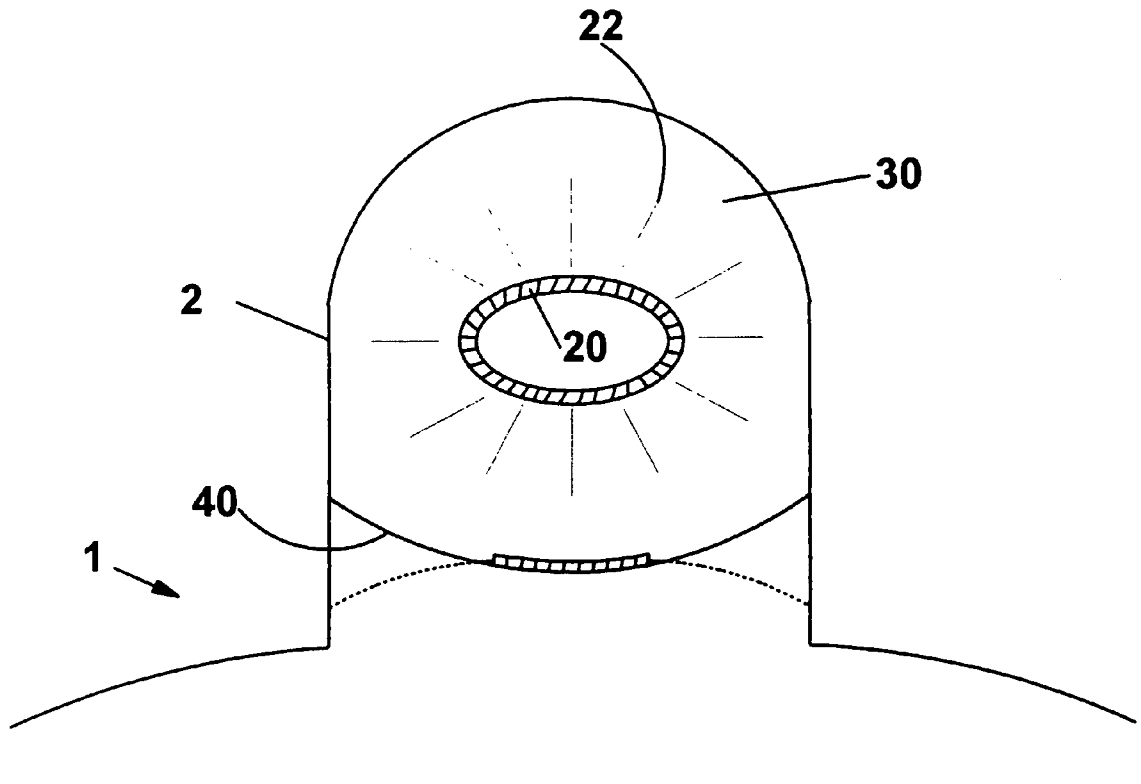
FIG. 3 shows an inside view of the cone shaped device within the head portion of FIG. 2 along arrow 2X before the cone shaped device is attached to the face mask.

FIG. 3 shows an inside view of the cone shaped device 18 within the head portion 2 of FIG. 2 along arrow 2X before the cone shaped device 18 is attached to the face mask 12. In the first embodiment, the novel cone shaped device 18 can be pre-attached to the inside of the head portion of a bio hazard type suit 1, so that the user only has to stretch the elastic end 20 of the cone shaped device 18 over their face mask 12 (shown in FIG. 2) when the user is putting on the suit 1.

Figure 4:
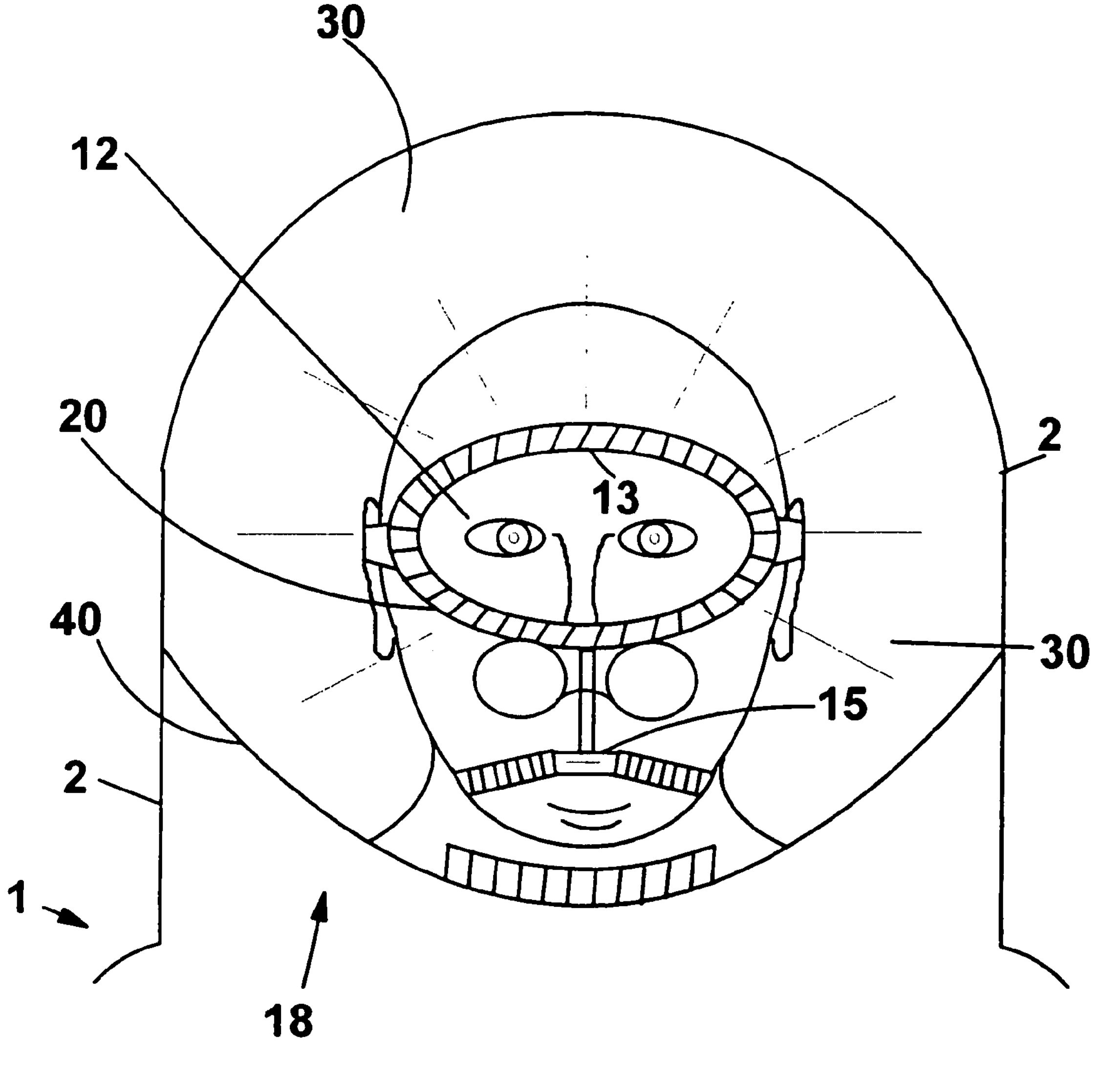
FIG. 4 is a front view of the body suit, novel cone space device, mask and worker of FIG. 2 along arrow 4X.

FIG. 4 is a front view of the body suit 1, novel cone space device 18, mask 12 and worker of FIG. 2 along arrow 4X. The cone shaped device 10 allows for the worker to have an unrestricted view since the cone shaped mid portion 30 can be formed from a flexible see-through plastic sheet, and the like, so that the worker's view is not obstructed therethrough.

Figure 5:
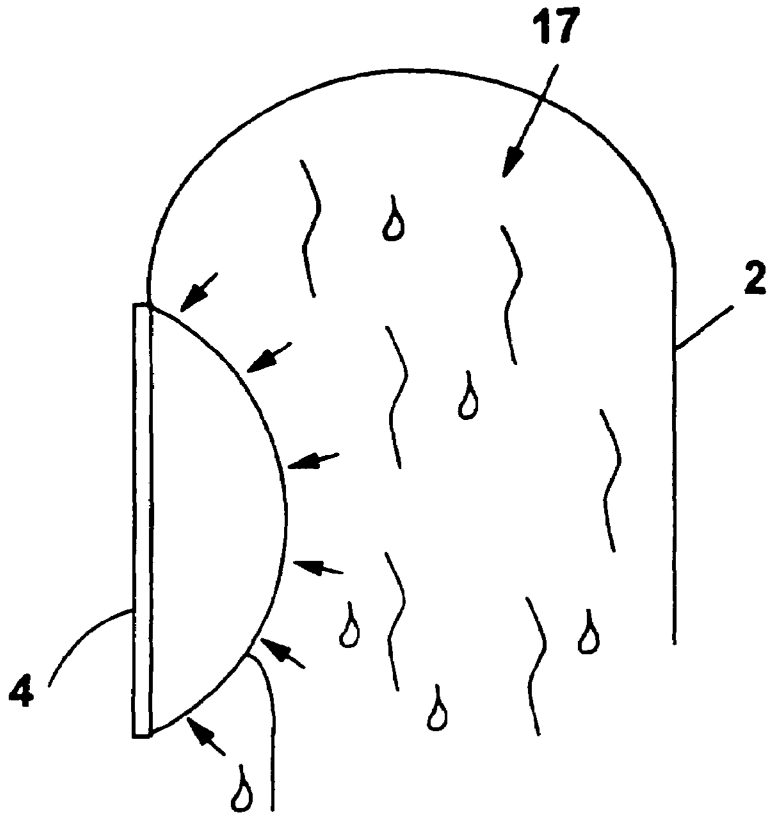
FIG. 5 is an exterior side view of moisture forming on the bio hazard suit and not on the exterior window visor of the suit.
Figure 6:
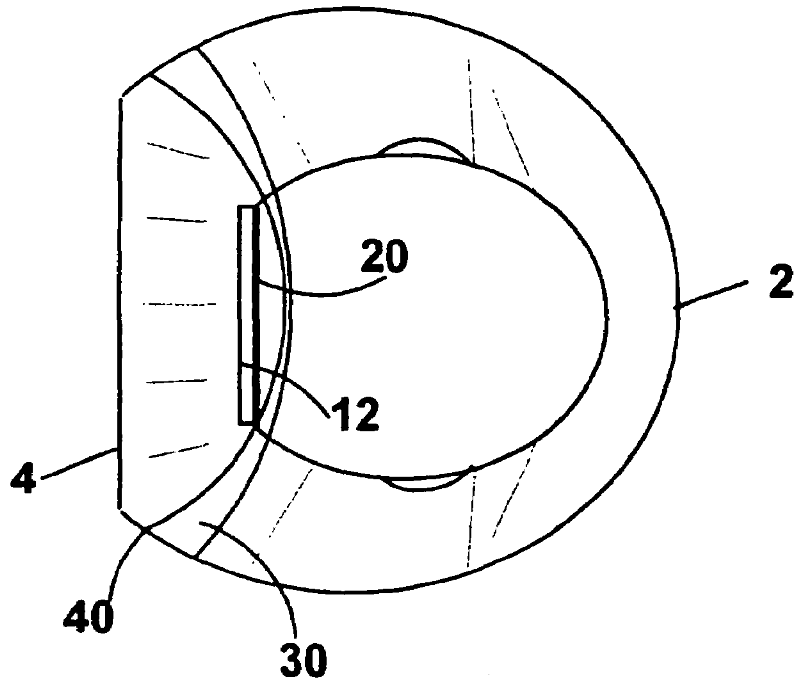
FIG. 6 is a top view of FIG. 2 along arrow 6Y, with the cone device forming a dry chamber that is between the face mask and the window visor of the head portion of the suit.

FIG. 5 shows a side view of moisture 17 such as condensation forming on the bio hazard suit head portion 1 and not on the window visor 4 of the suit 1. In many bio hazard suits, the window can have a rectangular or oval configuration. Here, the novel cone shaped device 18 forms a closed air space between the face mask visor 12 and the window visor 4 on the bio hazard suit 1. FIG. 6 shows a top cross-sectional view of the worker, cone space device 18 which forms a dry chamber within the cone shaped midportion 30 between the face mask 12 and the window visor 4 of the head portion 2 of the suit 1. The dry closed air chamber prevents condensation from forming on the face mask visor 12 and the window visor 4 of the suit 1.

Referring to FIGS. 1–6, the flexible see-through plastic type membrane that allows the user of the bio hazard suit to be able to see through the closed air space. The sealed dry space chamber within the cone shaped device 18 effectively eliminates and prevents condensation and moisture from building up on the visor and mask.

Experiments of using the invention were conducted. A cone shaped device 18 created by the inventors was made of; one plastic sheet and duck tape. The cone was fastened with duck tape between the facemask and the window visor 4 of level A suit such as those described in the background section of the invention. The cone shaped device 18 was to form a closed air pocket in which no increase of humidity would occur. The experiments included tasks where a worker walking a distance of 30 feet carrying a chair wearing the level A suit with the novel cone shaped device 18. Two chairs were used and every third time the distance was walked without carrying a chair. The chairs weighed 35 lb. each.

The experiment tasks were estimated to represent a higher workload than the average tasks performed in a Level A suit. The task was chosen to accelerate the conditions and accelerate the generation of fog and condensation. The participator of the experiment was approximately 27 years old, 6'3 tall and weighs 190 lb. The experiment was performed on the parking lot at the back of Fire station 1, in downtown Orlando on Nov. 9, 2001 between approximately 1.30 pm and approximately 4 pm in the afternoon. The experiment was performed in direct sunlight. The temperature was approximately 81 degrees F. To simulate normal conditions as far as possible the participator wore sweatpants, socks, a t-shirt, and a sweatshirt underneath the level A suit. Each of the three runs was performed for 10 minutes. The time was measured with a stopwatch. The resting time between the runs were approximately 30 minutes and the suit used was sufficiently aired out.

Table 1 shows the results of experiments that indicated fogging and condensation forming on the window visor of the body suit having no protection. Table 1 shows that fogging and condensation appeared on the window visor of the body suit occurred after five minutes which clearly obscured the vision of the worker wearing the suit.

TABLE 1

Suit with No Protection

| Type | Time until fog appeared |
|---|---|
| Suit Window Visor | 5 minutes |
| Face Mask Visor | 5 minutes |

Table 2 shows the results of experiments that indicated fogging and condensation forming on the window visor of the body suit where anti-fogging spray Rainex® described in the background section of the invention was used. Table 2 shows that fogging and condensation appeared on the window visor of the body suit occurred after approximately seven minutes which clearly obscured the vision of the worker wearing the suit.

TABLE 2

| Rainex applied. | |
|---|---|
| Type | Time until fog appeared |
| Suit Window Visor | 7 minutes |
| Face Mask Visor | 7 minutes |

With the experiments shown in Tables 1 and 2, fog and condensation started to appear on the suit window visor after approximately five minutes. Visibility decreased further as the time passed by. At the end of the experiments, a considerable amount of fog was noticed on the inner face mask as well. Tables 1 and 2 showed that fog on the face mask and window visor of the suit occurred no later than approximately seven minutes after the worker started wearing the suit.

Table 3 shows the results of experiments that indicated fogging and condensation forming on the window visor of the body suit that used the novel cone shaped device of the subject invention. Table 1 shows that fogging and condensation appeared on the window visor of the body suit occurred after five minutes which clearly obscured the vision of the worker wearing the suit.

TABLE 3

| Cone applied. | |
|---|---|
| Type | Time until fog appeared |
| Suit Window Visor | 0.0 minutes |
| Face Mask Visor | 0.0 minutes |

In the experiment shown in Table 2, fog and condensation started to appear on the suit after approximately seven minutes. In the experiment with the cone applied, as shown in Table 3, no fog and no condensation were observed on the inner face mask or on the suit window visor at the end of the experiment.

The experiment ended after approximately twenty minutes, since twenty minutes is considered the maximum amount of time that is intended that a worker can usually wear a bio hazard type suit between breaks.

Additionally, firefighters are also only supposed to stay in bio hazard type suits for approximately twenty minutes a time, due to the air supply and the heat conditions that lead to dehydration.

The novel closed cone device invention maximizes the known fact that for rescue workers such as firefighters that every second is valuable. With the novel invention, the reduced time that a worker can wear their suit along with the reduction in for cleaning the face mask and the suit visor, the more time the firefighters can spend on the actual task.

In the experiments the novel cone device was able to keep the vision clear for the duration of the useful wearing time of the suit.

While the preferred embodiment described above referred to an elastic band such as a rubber type band to allow for the cone shaped device to be easily attached and removed from the facemask, other types of fasteners can be used. For example, hook and loop fasteners(Velcro®) can be used as an easy to use fastener to create a seal between the cone device and the face mask, where a strip of hook and loop fasteners can be pre-attached to both the face mask and the narrow end of the cone shaped device. Additionally, a zipper fastener can be located between the face mask and the cone shaped device to create a removable seal therebetween. Furthermore, snap fasteners can be used between the face mask and the cone shaped device to create a removable seal therebetween.

Although the preferred embodiment can use a pre-sealed attachment between the cone shape device and the inside of the window visor of the suit, the invention can be used with an easy to attach and remove fasteners therebetween. For example, hook and loop fasteners(Velcro®) can be used as an easy to use fastener to create a seal between the cone device and the inner surface of the window visor of the suit, where a strip of hook and loop fasteners can be pre-attached to both the inside of the window visor of the suit and the wide end of the cone shaped device. Additionally, a zipper fastener can be located between the inside of the window visor of the suit and the cone shaped device to create a removable seal therebetween. Furthermore, snap fasteners can be used between the window visor of the suit and the cone shaped device to create a removable seal therebetween.

Second Embodiment

Figure 7:
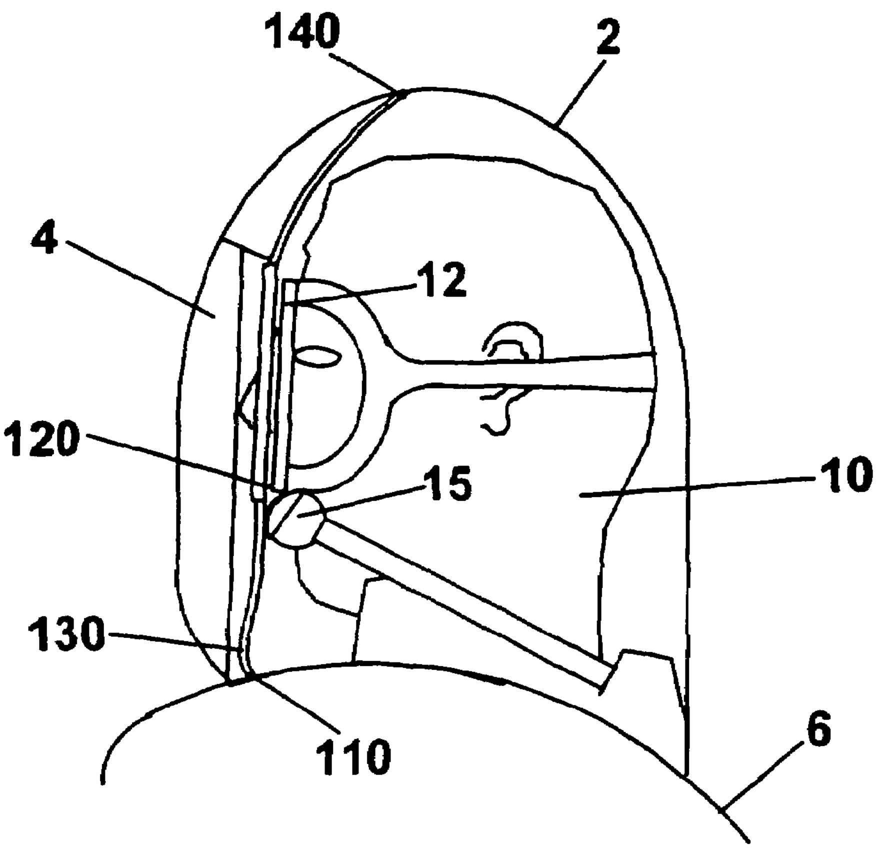
FIG. 7 is a side cross-sectional view of a second embodiment using a flat flexible plastic see-through sheet device to form the closed space between the mask and the suit window.
Figure 8:
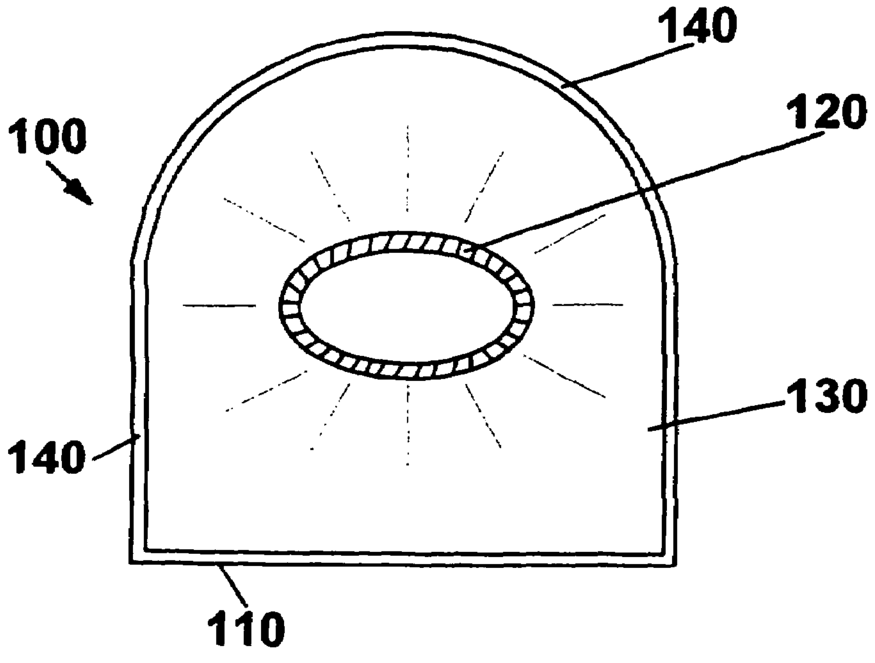
FIG. 8 is a front view of the sheet device of FIG. 7.

FIG. 7 is a side cross-sectional view of a second embodiment using a flat flexible plastic see-through sheet device 100 to form the closed space between the face mask 12 and the suit window visor 4. FIG. 8 is a front view of the sheet device 100 of FIG. 7.

Referring to FIGS. 7–8, the second embodiment sheet device 100 can have an upper inverted U-shape with an upper perimeter edge 140 that can be presealed against the interior surface of the head portion 2 of the suit by vulcanizing techniques, sewn, and the like. The sheet device 100 can include a see-through plastic flexible material 130 similar to the material described in the previous embodiment, and include a generally centrally located oval opening having an elastic band type fastener 120 similar to that of the first embodiment, in order to allow for the device 100 to be easily wrapped about the perimeter edge of the face mask 12 of the worker 10. The lower part of the second embodiment device 100 can include a slightly concaved lower edge with fastener strip 110 that can easily fasten to the front chest portion of the bottom half of the suit 6.

Fastener strip 110 can allow for a worker to easily attach and remove the sheet device 100 to the lower half chest portion of the suit 6. For example, hook and loop fasteners (Velcro®) on both the strip 110 and on the chest area of the lower half of the suit 6, can be used as an easy to use fastener to create a seal between the lower half of the sheet device 100 and the chest area of the suit. Additionally, a zipper fastener strip 110 can sealingly attach the sheet device 100 to a mateable zipper strip on the chest area of the body suit 6. Furthermore, snap fasteners can also be used at 110 and on the chest area of the suit 6 to create a removable seal therebetween.

Similar to the first embodiment, the second embodiment creates a closed air space between the face mask 12 and the window visor 4 of the suit that prevents condensation such as fogging from forming on the face mask 12 and on the window visor 4 of the suit.

Another version of the second embodiment can allow for a removable fastener strip to be used in place of the presealed edge 140. Such as removable fastener strip can include hook and loop fasteners, zipper(s), and/or snap fasteners as previously described to form a removal sealed edge.

Third Embodiment

Figure 9:
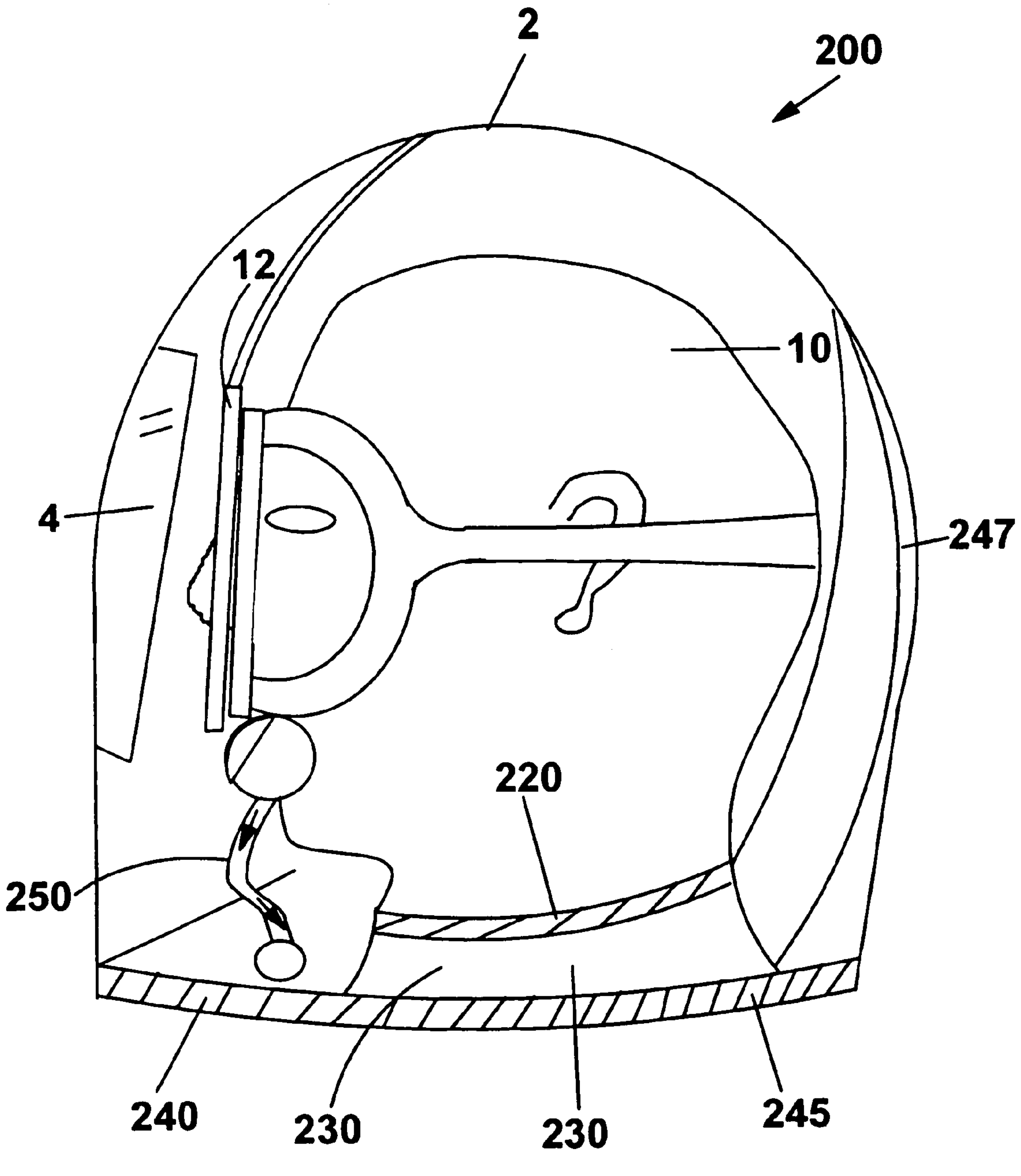
FIG. 9 is a side cross-sectional view of a third embodiment using neck inserted sheet bag for forming the closed air space between the face mask and the window of the suit.

FIG. 9 is a side cross-sectional view of a third embodiment 200 using neck inserted sheet bag 230 of a flexible plastic see-through material, for forming the closed air space between the face mask 12 and the window visor 4 of the suit. Here a lower edge of the sheet bag 200 can have an edge 240 that is pre-sealed to a lower edge of the head portion 2 of the suit by vulcanizing techniques, sewn, and the like. The lower edge 240 can fit over the upper shoulder portions of the worker and can seal about the entire lower edge of the head portion 4 as shown by lower edge 240, 245. A mid portion of the bag 220 can have an elastic type band such as those previously described that the worker sticks their bead 10 through so that a seal exists about the neck of the worker 10. The worker 10 can also use a flexible moist exhaust air vent line 250 such as a tube that allows for moist air to exit from inside to outside the head portion 2 or the suit. This embodiment allows for the worker 10 to have no extra materials inside of the head portion 2 of the suit.

Thus, the closed space can be formed by creating an elastic neck portion on the bio hazard suit below the regular head gear worn by a worker. As shown, the neck portion of the bio hazard suit can include an elastic type band portion that wraps about the neck of the user and further helps seal off the air space in the head gear portion of the bio hazard suit.

The back of the sheet bag 230 can also be pre-sealed(by vulcanizing techniques, sewn, and the like) to an inner surface portion of the head portion 2 of the suit behind the worker 10 as shown by strip 247.

Still furthermore, the lower edges 240, 245, 247 can also include a removable seal fastener(s) such as but not limited to strips of hook and loop fasteners, zipper(s), and snap fasteners, such as those described in the previous embodiments.

Although the preferred embodiments are described with hazard material and bio hazard type suits, the invention can also be used with other types of suits where condensation and fogging are a problem, such as but not limited to diving suits, outer space suits for astronauts, and the like.

The invention can be built into the above suits during the initial manufacturing of the suits. Alternatively, the suits can be retrofitted with the invention at a later time. The invention can be made and sold as a kit for modifying suits, and the like.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

We claim:

1. A method of eliminating fogging effects on a face mask worn by a person wearing a full body and head suit with window, comprising the steps of:

providing a flexible plastic housing having a first and a second end each having a detachable fastener;

sealingly wrapping the detachable fastener of the first end to the face mask and the second end to the window of the suit to form a closed air space between the face mask and the window of the suit so that the flexible plastic housing is removably attached; and eliminating condensation from forming on the face mask and the window as the suit is being worn during an emergency condition with the closed air space.

2. The method of claim 1, wherein the step of providing includes the step of:

forming the flexible plastic housing from cone shaped flexible see-through plastic.

3. The method of claim 1, comprising the step of:

stretching an end portion of the flexible plastic housing forming the closed air space about a perimeter portion of the face mask with an elastic member to form an air seal therebetween.

4. The method of claim 1, wherein the eliminating step further includes the step of:

eliminating the condensation from forming up to approximately 20 minutes of wearing the suit.

5. The method of claim 1, further comprising the step of:

stretching a central cut-out portion of the sheet about a perimeter portion of the face mask with an elastic member to form an air seal therebetween.

6. The method of claim 1, further comprising the step of:

exhausting moist air from the face mask to outside the bag.

* * * * *